US011744479B2

(12) United States Patent
Izmirli et al.

(10) Patent No.: US 11,744,479 B2
(45) Date of Patent: Sep. 5, 2023

(54) MULTI-LAYER FLAT COIL MAGNETIC TRANSMITTERS

(71) Applicant: St. Jude Medical International Holding S.à r.l., Luxembourg (LU)

(72) Inventors: Alon Izmirli, Ganot Hadar (IL); Yuval Vaknin, Hanaton (IL); Guy Hevel, Zicron Yaakov (IL); Adrian Herscovici, Or Akiva (IL); David Jacobs, Nahariya (IL)

(73) Assignee: ST JUDE MEDICAL INTERNATIONAL HOLDING, SA.R.L., Luxembourg (LU)

( * ) Notice: Subject to any disclaimer, the term of this patent is extended or adjusted under 35 U.S.C. 154(b) by 1148 days.

(21) Appl. No.: 16/461,283

(22) PCT Filed: Dec. 13, 2017

(86) PCT No.: PCT/IB2017/001660
§ 371 (c)(1),
(2) Date: May 15, 2019

(87) PCT Pub. No.: WO2018/109555
PCT Pub. Date: Jun. 21, 2018

(65) Prior Publication Data
US 2020/0054242 A1 Feb. 20, 2020

Related U.S. Application Data

(60) Provisional application No. 62/433,774, filed on Dec. 13, 2016.

(51) Int. Cl.
*A61B 5/06* (2006.01)
*A61B 6/04* (2006.01)
(Continued)

(52) U.S. Cl.
CPC ............ *A61B 5/062* (2013.01); *A61B 6/0407* (2013.01); *A61B 6/487* (2013.01);
(Continued)

(58) Field of Classification Search
None
See application file for complete search history.

(56) References Cited

U.S. PATENT DOCUMENTS 5,471,142 A 11/1995 Wang
7,386,339 B2 6/2008 Strommer et al.
(Continued)

FOREIGN PATENT DOCUMENTS

CN 102998641 A 3/2013
CN 104720803 A 6/2015
(Continued)

*Primary Examiner* — Shahdeep Mohammed
(74) *Attorney, Agent, or Firm* — Billion & Armitage (57) ABSTRACT

A magnetic field generator assembly is configured to be associated with a table supporting a body. The magnetic field generator comprises a plurality of magnetic field transmitters, each comprising interlacing layers of conductive material, configured to provide increased magnetic strength and minimal fluoroscopic occlusion. The interlacing layers of conductive material can be arranged in rectangular spiral formations.

18 Claims, 8 Drawing Sheets

(51) Int. Cl.
    *A61B 6/00*           (2006.01)
    *G01R 33/38*         (2006.01)
    *A61B 34/20*         (2016.01)
    *G01R 33/34*         (2006.01)
    *A61B 90/00*         (2016.01)

(52) U.S. Cl.
    CPC ... *G01R 33/34038* (2013.01); *G01R 33/3808* (2013.01); *A61B 2034/2051* (2016.02); *A61B 2090/363* (2016.02); *A61B 2090/376* (2016.02)

(56) References Cited

U.S. PATENT DOCUMENTS

| | | |
|---|---|---|
| 2008/0183071 A1 | 7/2008 | Strommer et al. |
| 2010/0109848 A1 | 5/2010 | Blair et al. |
| 2010/0305427 A1 | 12/2010 | Huber et al. |
| 2012/0029343 A1 | 2/2012 | Wasson et al. |
| 2012/0197108 A1* | 8/2012 | Hartmann ............ A61B 6/4405 600/424 |
| 2013/0016021 A1* | 1/2013 | Blair .................... H01Q 21/061 343/720 |
| 2015/0216490 A1 | 8/2015 | Ashe |
| 2017/0360514 A1 | 12/2017 | Eichler et al. |

FOREIGN PATENT DOCUMENTS

| | | |
|---|---|---|
| CN | 105813560 A | 7/2016 |
| CN | 105979866 A | 9/2016 |
| CN | 106037742 A | 10/2016 |
| WO | 2012/090148 A1 | 7/2012 |
| WO | 2015/068069 A1 | 5/2015 |

* cited by examiner

MULTI-LAYER FLAT COIL MAGNETIC TRANSMITTERS

CROSS-REFERENCE TO RELATED APPLICATIONS

This application claims the benefit of U.S. provisional application No. 62/433,774, filed 13 Dec. 2016, which is hereby incorporated by reference in its entirety as though fully set forth herein.

BACKGROUND a. Field

The present disclosure relates to thin, multi-layered, interlaced magnetic field transmitters configured to, among other things, increase magnetic strength and minimally occlude a fluoroscopic image.

b. Background

A wide variety of medical devices may be inserted into the body to diagnose and treat various medical conditions. Catheters, for example, are used to perform a variety of tasks within human bodies and other bodies, including the delivery of medicine and fluids, the removal of bodily fluids, and the transport of surgical tools and instruments. In the diagnosis and treatment of atrial fibrillation, for example, catheters may be used to deliver electrodes to the heart for electrophysiological mapping of the surface of the heart and to deliver ablative energy to the surface of the heart.

Catheters are typically routed to a region of interest through the body's vascular system. In a conventional catheterization, a micro-puncture needle (e.g., a Seldinger needle) is used to puncture the skin surface to gain access to, for example, a femoral artery, and a guide wire is then inserted through the needle before the needle is removed. A catheter sheath with a dilator inserted in it is then inserted over the guide wire. The dilator and the guide wire are then removed, leaving the sheath in place in the femoral artery. The sheath has an inner diameter greater than the outer diameter of a catheter to be used in the procedure. The catheter is then inserted into the sheath, and the sheath and/or catheter are subsequently threaded through the vasculature to a region of interest. Typically, but not necessarily, the catheter is then moved longitudinally relative to the sheath so as to extend from the distal end of the sheath to the region of interest. The longitudinal movement may be done either manually by a clinician or through the use of electromechanical drive systems.

It is desirable to track the position of medical devices such as catheters as they are moved within the body so that, for example, drugs and other forms of treatment are administered at the proper location and medical procedures can be completed more efficiently and safely. One conventional means to track the position of medical devices within the body is fluoroscopic imaging. Fluoroscopy is disadvantageous, however, because it subjects the patient and physician to undesirable levels of electromagnetic radiation. As a result, medical device navigation systems have been developed to track the position of medical devices within the body. These systems typically rely on the generation of electrical or magnetic fields and the detection of induced voltages and currents on position sensors attached to the medical device and/or external to the body. The information derived from these systems is then provided to a physician through, for example, a visual display. Oftentimes, a representation of the medical device is displayed relative to a computer model or one or more images (including, but not limited to, fluoroscopic images) of the anatomical region in which the device is being maneuvered. In order to display the medical device at the correct location relative to the model or image, the model or image must be registered within the coordinate system of the navigation system.

Magnetic field transmitters may be used in conjunction with a medical device navigation system. The transmitters within the navigation system can be installed in a variety of ways. If the imaging system used to capture the images is physically integrated with the navigation system, as described in commonly assigned U.S. Published Patent Application No. 2008/0183071 A1, the entire disclosure of which is incorporated herein by reference, the transmitters can be installed such that they will not be in the path of the x-ray beam. The foregoing discussion is intended only to illustrate the present field and should not be taken as a disavowal of claim scope.

BRIEF SUMMARY OF THE DISCLOSURE

The present disclosure describes a magnetic field generator assembly configured to be associated with a table supporting a body. The magnetic field generator comprises a plurality of magnetic field transmitters, each comprising interlacing layers of conductive material, configured to provide increased magnetic strength and minimal fluoroscopic occlusion. The interlacing layers of conductive material can be arranged in rectangular spiral formations.

In an embodiment, a magnetic field generating assembly, configured to be associated with a table supporting a body, the assembly comprises: a first plurality of elongate conductive elements arranged in a first plane, wherein each of the first plurality of elongate conductive element winds around a first central axis, extending perpendicular to the first plane, in a first spiral formation; and a second plurality of elongate conductive elements arranged in a second plane, the second plane being substantially parallel to the first plane, wherein each of the second plurality of elongate conductive element winds around a second central axis, extending perpendicular to the second plane, in a second spiral formation; wherein each of the first plurality of elongate conductive elements is interlaced with a corresponding one of the second plurality of elongate elements; and wherein each of the first plurality of elongate conductive elements is electrically connected to the corresponding one of the second plurality of elongate conductive elements.

In another embodiment, a medical device navigation system comprises: a magnetic field generator assembly configured to be used in close proximity to a body undergoing treatment, wherein the magnetic field generator assembly comprises: a first plurality of elongate conductive elements arranged in a first plane, wherein each of the first plurality of elongate conductive element winds around a first central axis, extending perpendicular to the first plane, in a first spiral formation; and a second plurality of elongate conductive elements arranged in a second plane, the second plane being substantially parallel to the first plane, wherein each of the second plurality of elongate conductive element winds around a second central axis, extending perpendicular to the second plane, in a second spiral formation; a conductive wire connecting the first and second pluralities of conductive elements to a power source; a control unit capable of controlling current supplied to the first and second pluralities of conductive elements; and a housing surrounding the first and second pluralities of conductive elements; wherein each of the first plurality of elongate conductive elements is interlaced with a corresponding one of the second plurality of elongate elements; and wherein each of the first plurality of elongate conductive elements is electrically connected to the corresponding one of the second plurality of elongate conductive elements.

The foregoing and other aspects, features, details, utilities, and advantages of the present disclosure will be apparent from reading the following description and claims, and from reviewing the accompanying drawings.

DETAILED DESCRIPTION

Figure 1:
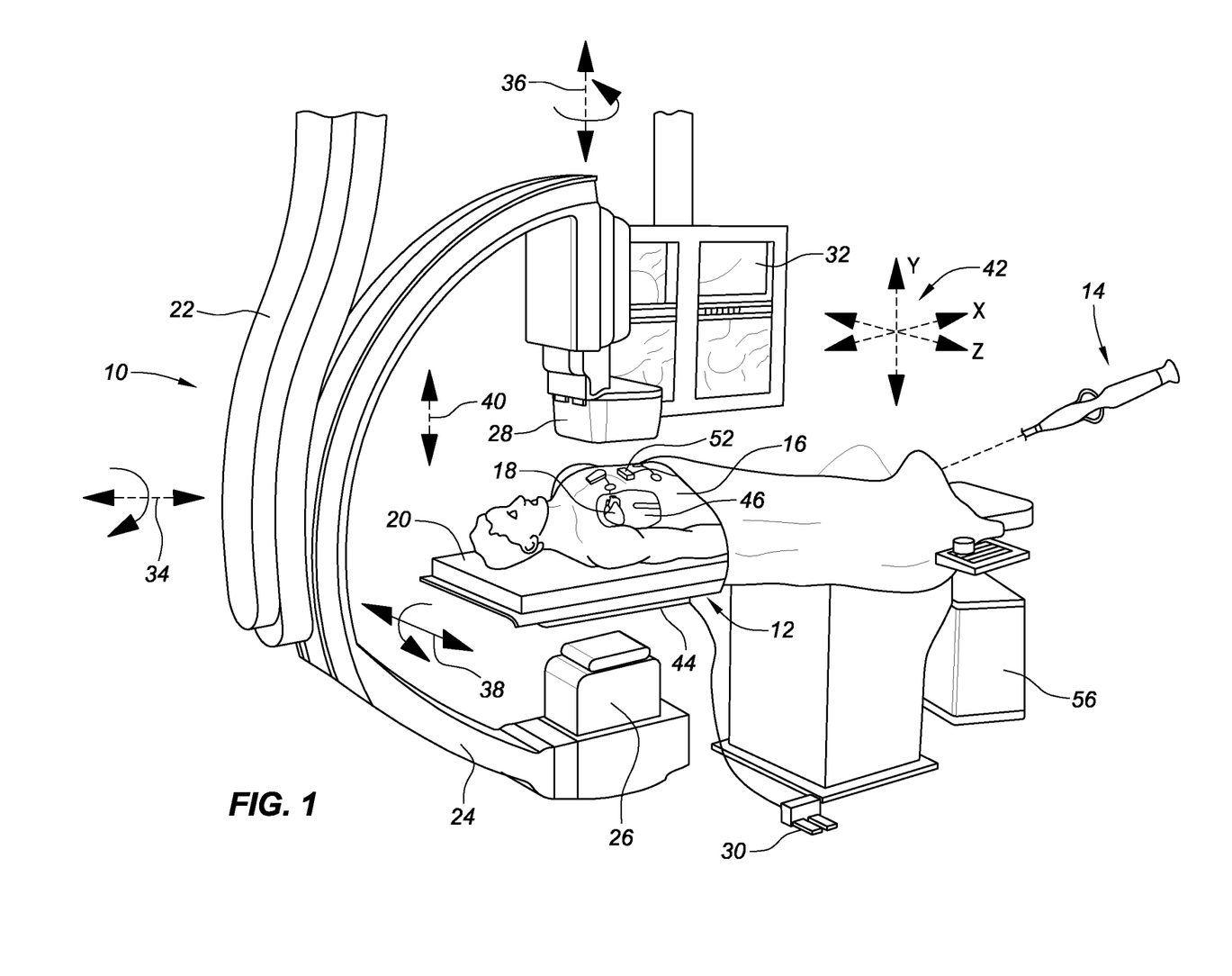
FIG. 1 is a diagrammatic view of a medical device navigation system in accordance with one embodiment of the present teachings.

Referring to the drawings wherein like reference numerals are used to identify identical components in the various views, FIG. 1 illustrates an electrophysiology lab including an imaging system 10 and a system 12 for navigating a medical device 14 relative to and within a region of interest in a patient's body 16 such as the heart 18 in accordance with one embodiment of the present teachings. Device 14 may comprise, for example, an electrophysiological (EP) mapping catheter, an intracardiac echocardiography (ICE) catheter, or an ablation catheter. It should be understood, however, that the inventive system could be used to navigate a variety of diagnostic and treatment devices used to treat various regions of interest within body 16.

Imaging system 10 is provided to acquire images of heart 18 or other anatomical regions of interest and comprises a fluoroscopic imaging system in the illustrated embodiment. System 10 has a structure that is movable relative to the various components of system 12 and relative to body 16 and a table 20 supporting body 16. System 10 may include a number of structural components including, in the illustrated embodiment, a support 22, an arm 24, a radiation emitter 26, and a radiation detector 28. System 10 may also include an electronic control unit (not shown) for controlling operation of system 10 and one or more input devices such as control pedal 30 and output devices such as display 32.

Support 22 provides a means for supporting arm 24 and for moving arm 24, emitter 26, and detector 28 relative to body 16. In the illustrated embodiment, support 22 is suspended from a ceiling in the EP lab. Support 22 may be affixed to rails (not shown) or similar structures and may be moved by mechanical, electrical, or electromechanical devices (not shown). Support 22 may be configured to rotate with arm 24, emitter 26, and detector 28 about an axis 34 to position arm 24, emitter 26, and detector 28 relative to body 16.

Arm 24 provides a means for supporting emitter 26 and detector 28 relative to body 16. Arm 24 may be substantially C-shaped (i.e., a "C-arm") to provide sufficient clearance relative to body 16 and table 20. Arm 24 is configured to rotate in either direction about an axis 36 relative to support 22 to cause corresponding movement of emitter 26 and detector 28 and position emitter 26 and detector 28 relative to body 16 to permit images to be acquired from a variety of angles or orientations.

Emitter 26 is provided to emit electromagnetic radiation (e.g., x-rays) over a field of view between emitter 26 and detector 28 including the anatomical region of interest in body 16. Emitter 26 is disposed at one end of arm 24.

Detector 28 captures electromagnetic radiation passing through the anatomical region of interest in body 16 and generates signals used to create images of the region of interest. In one embodiment, detector 28 may comprise a flat detector and may be configured to rotate about an axis 34 relative to arm 24 and may also be movable relative to arm 24 along an axis 40 to vary the distance between the emitter 26 and detector 28 (i.e., the "source to image" distance or "SID"). Detector 28 is disposed at an opposite end of arm 24 relative to emitter 26.

The relative movement of imaging system 10 and other objects within the electrophysiology lab create various degrees of freedom that system 12 may need to account for as a physician navigates device 14. Arm 24 rotates about axes 34, 36, and 38, and moves along axis 40. Table 20 may move relative to imaging system 10 (or vice versa) in either direction along three orthogonal axes resulting in as many as seven degrees of freedom.

Control pedal 30 provides a means for the physician to control imaging system 10. The physician may, for example, depress pedal 30 to activate radiation emitter 26. Pedal 30 may communicate with an electronic control unit (not shown) for imaging system 10 via a wired or wireless connection.

Display 32 is provided to convey information to a physician to assist in diagnosis and treatment. Display 32 may comprise one or more computer monitors or other display devices. Display 32 may present fluoroscopy images and a graphical user interface (GUI) to the physician. The GUI may communicate a variety of information including, for example, an image of the geometry of heart 18, electrophysiology data associated with the heart 18, graphs illustrating voltage levels over time for various electrodes on medical device 14, and images of medical device 14 and related information indicative of the position of device 14 and other devices relative to the heart 18.

System 12 may be used to determine the position of device 14 within body 16 and within a coordinate system 42 and to navigate device 14 within body 16. System 12 may also be used to determine the positions of other movable objects within the EP lab within coordinate system 42 including body 16 and table 20.

In accordance with one embodiment of the present teachings, system 12 is also used to determine the position of imaging system 10 within coordinate system 42 and, in particular, various components of imaging system 10. System 12 employs magnetic fields and may comprise the system made available under the trademark MediGuide™ by St. Jude Medical, Inc. and generally shown and described in, for example, commonly owned U.S. Pat. No. 7,386,339 and U.S. patent application Ser. No. 61/787,542, the entire disclosures of which are incorporated herein by reference. System 12 may include a magnetic field generator assembly 44 (shown to better advantage in FIG. 2), means (such as position sensors 46 and 52) for generating information regarding the position of device 14 within body 16 and the position of various objects in the EP lab such as imaging system 10, body 16, and table 20. System 12 may also include an electronic control unit (ECU) 56 and a display such as display 32.

Figure 2:
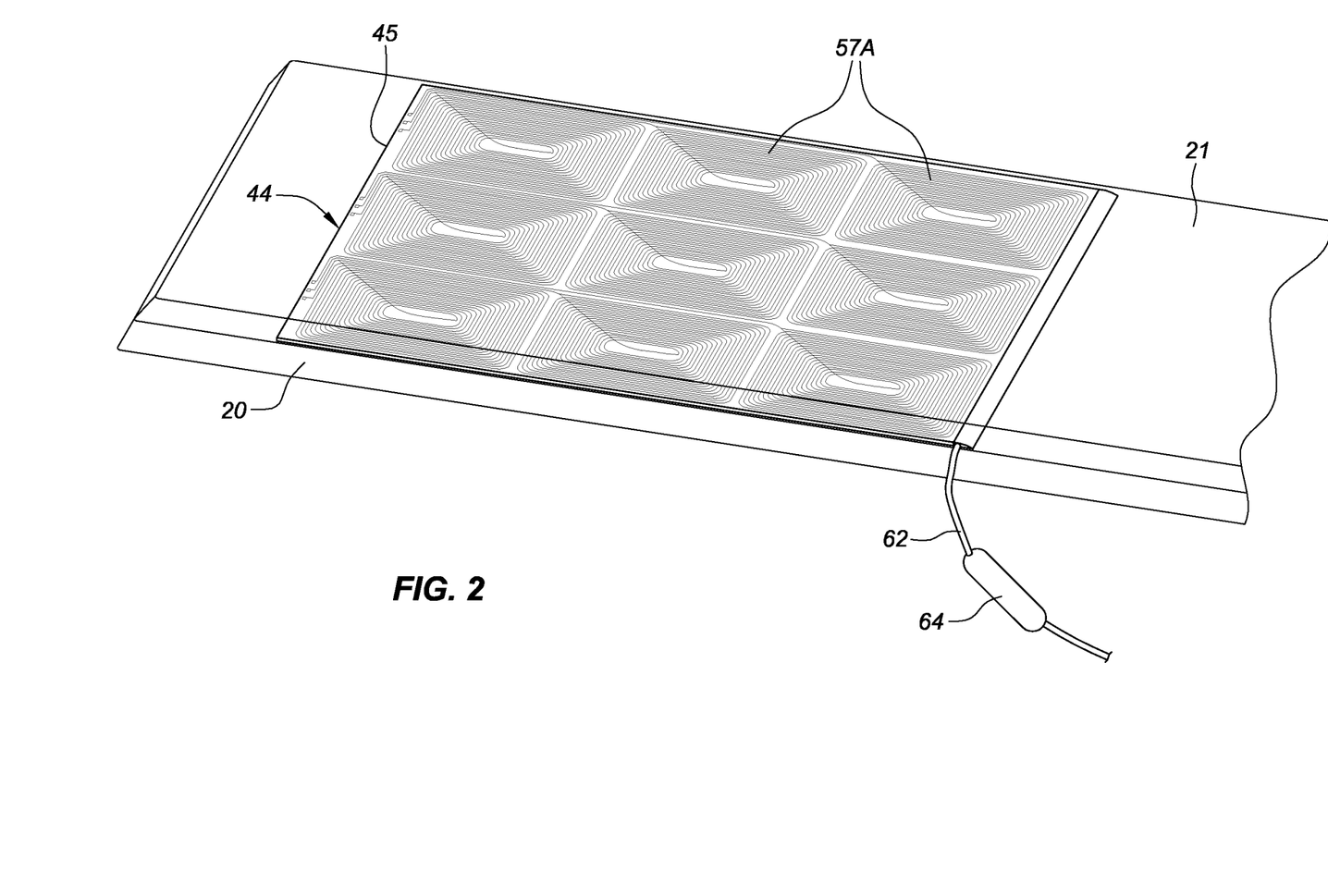
FIG. 2 is a diagrammatic view of the magnetic field generator assembly of the system of FIG. 1.

Generator assembly 44 generates magnetic fields that cause a response in sensors 46 and 52 indicative of the location and orientation of sensors 46 and 52 within the magnetic fields and within coordinate system 42. Generator assembly 44 may be located just beneath table 20, as shown in FIG. 1. Alternatively, generator assembly 44 may be located on top of table 20, such that generator assembly 44 is between a mattress 21 and table (as shown in FIG. 2) and/or between body 16 and table 20. Generator assembly 44 may also be located within table 20 and/or mattress 21. In another embodiment, a generator assembly similar to assembly 44 may be located directly on a patient's body using one or more patches, for example, such as those similar to EnSite™ NavX™ surface electrode patches sold by St. Jude Medical, Inc. Generator assembly 44 may also be installed, so as not to significantly occlude the path of the x-ray beam, in systems where the navigation and imaging systems are physically separate, as described in commonly assigned U.S. patent application Ser. No. 61/787,542.

Referring to FIG. 2, generator assembly 44 may comprise magnetic field transmitters, such as transmitters 57A, positioned within a housing 45 (or, alternatively, the transmitters may be positioned on the housing). In an embodiment, a plurality of transmitters 57A can be used, such as the nine transmitters 57A arranged in a 3×3 pattern as shown. Alternative patterns can also be used. Each transmitter 57A can comprise an elongate conductive element, such as a wire, arranged in a spiral form, such as a coil. The wire gauge used to make the spiral coils of transmitters 57A can be about 0.7 mm (width) by 1 oz. (thickness). The typical length of the wires can be about 20 meters. The separation distance between adjacent turns of the coils of transmitters 57A can be about 0.3 mm. The spiral coils of transmitters 57A can be rectangular in shape to occupy the majority of the generator assembly 44 and leave very little space unoccupied, as shown in FIG. 2. Alternatively, transmitters may be circular in shape. Regardless, in at least one embodiment, the transmitters may be thin and flat, such that they can be easily integrated into or associated with table 20. In an embodiment, the height of each transmitter can typically range from about 10 micrometers to about 0.25 millimeters. Moreover, the distance between the transmitters and the housing 45 that forms the exterior of the generator assembly is minimal, ranging from about 0.2 mm to 2 cm, and the housing 45 may be about 0.2 mm to 2 cm in total height, about 10 cm to 50 cm in total width, and about 10 cm in total length. Thus, generator assembly 44 may be thin and substantially flat. As such, generator assembly 44 may be placed under a mattress 21 or table 20 with minimal or no impact on the geometry of arm 24 and the path in which arm 24 may move relative to bed 20 during a procedure.

Since transmitters (such as transmitters 57A discussed above with respect to FIG. 2, as well as transmitters 57B and 57C discussed below with respect to FIGS. 3 and 4, respectively) according to the disclosed teachings are substantially thin and flat, they also are transparent to, or nearly transparent to, x-rays, which reduces the potential for fluoroscopic interference. As used in this disclosure, "nearly transparent" can mean minimally occlusive (e.g., forming minimal and/or uniform background artifact), or substantially invisible to the human eye, in fluoroscopic images. In an embodiment, transparent or nearly transparent transmitters should not require more radiation to be used in system 10 than would be necessary if the transmitters were absent. As such, the transmitters are configured to be substantially thin and flat and to minimally occlude fluoroscopic images. At the same time, however, the transmitters need to be thick enough to be conductive. Materials that have been found to best meet this compromise include aluminum, copper, graphene, and magnesium. Thus, in an embodiment, the transmitters are made from a thin layer of copper, aluminum, graphene, magnesium, or other conductive material. Additionally, the transmitters may be encapsulated in x-ray transparent material, such as one or more layers of carbon fiber. In some embodiments, the transmitters may be enclosed in a carbon fiber box or housing.

As further shown in FIG. 2, cable 62 provides a means for connecting assembly 44 to ECU 56. Accompanying electronics 64 can be placed on and communicate with cable 62. Accompanying electronics 64 can be used to filter electromagnetic signals going to/from transmitters and resonance circuitry, for example.

Referring again to FIG. 1, position sensors 46 and 52 provide a means for generating information regarding the position of various objects within coordinate system 42. As sensors 46 and 52 move within the magnetic field generated by generator assembly 44, the current output of each sensor 46 and 52 changes, thereby indicating the location of sensors 46 and 52 within the magnetic field and within coordinate system 42. Position sensors 46 and 52 may comprise coils. Sensor 46, for example, may be wound about device 14 at or near distal end of device 14, embedded within a wall of device 14, or within a cavity within device 14. Sensors 46 and 52 may also have appropriate insulation and/or shielding (e.g., a conductive foil or wire mesh) to cancel potential interferences from other devices near body 16.

In alternative embodiments, sensors 46 and 52 may comprise any position sensors for detecting changes in magnetic fields including, for example, Hall effect sensors, magnetoresistive sensors, and sensors made from magnetoresistive materials and piezoelectric materials and the like. Sensors 46 and 52 may also be of a type that is able to sense position in one or more (e.g., 1 to 6) degrees of freedom relative to a field generator. Sensors 46 and 52 may communicate position signals to ECU 56 through an interface (not shown) using wires or other conductors, or wirelessly.

In accordance with another embodiment of the present teachings, information regarding the position of imaging system 10 may be obtained based on inputs to or outputs from the imaging system 10. In one embodiment, image data output to display 32 or another destination may be captured and read by ECU 56. The position of imaging system 10 may be determined based on fiducial markers in the image or through use of optical character recognition or other techniques for reading character data imprinted on the image and indicative of the position of imaging system 10 or a component thereof, relative to either a prior position of the component or another component of imaging system 10. In particular, the fiducial markers may be embedded in the magnetic field generator assembly 44.

In accordance with yet another embodiment of the present teachings, information regarding the position of imaging system 10 and/or other information associated with imaging system 10 may be obtained by sensing the activation of imaging system 10 and, in particular, the emission of radiation from emitter 26. Radiation emissions may be detected using a radiation detection sensor such as the XB8816 Series sensor offered for sale by X-Scan Imaging Corporation. These sensors maybe embedded in magnetic field generator assembly 44. ECU 56 may be configured to determine a time associate with the radiation emission responsive to a signal generated by the radiation detector sensor and thereby synchronize signals generated by other sensors such as position sensors 46 and 52.

In accordance with yet another embodiment of the present teachings, information regarding the position of imaging system 10 may be obtained by detecting objects, such as anatomical or artificial fiducials, in images generated by system 10 that have a known position within coordinate system 42. In particular, these objects may be embedded in magnetic field generator assembly 44. To limit interference with the physician's view of the anatomy, these objects may have multiple states whereby the objects are visible in some images and invisible in others, or may be generally undetectable to the human eye, but detectable through image processing as described in greater detail in PCT International Publication No. WO 2012/090148 A1, the entire disclosure of which is incorporated herein by reference. In some configurations, the transmitter wiring in magnetic field generator assembly 44 may be undetectable to the human eye, but detectable through image processing.

Although various embodiments have been disclosed above for obtaining positioning information regarding imaging system 10, it should be understood that elements of multiple embodiments could be used in combination. Referring again to FIG. 1, ECU 56 provides a means for determining the position of sensors 46 and 52—and the objects to which sensors 46 and 52 are attached—within coordinate system 42. As discussed below, ECU 56 may further provides a means for registering images generated by imaging system 10 in coordinate system 42 and superimposing images of device 14 on such images, a means for comparing the positions of various objects in the EP lab (such as imaging system 10 and generator assembly 44 or body 16 or table 20) to determine potential physical interference, and/or a means for providing information about the positions of various objects to a physician or other user of system 12. ECU 56 also provides a means for controlling the operation of various components of system 12, including magnetic field generator assembly 44. In embodiments where medical device 14 comprises an electrophysiology or ablation catheter, ECU 56 may also provide a means for controlling device 14 and for determining the geometry of heart 18, electrophysiology characteristics of heart 18 and the position and orientation of device 14 relative to heart 18 and body 16. ECU 56 may also provide a means for generating display signals used to control a display such as display 32. ECU 56 may comprise one or more programmable microprocessors or microcontrollers or may comprise one or more application specific integrated circuits (ASICs). ECU 56 may include a central processing unit (CPU) and an input/output (I/O) interface through which ECU 56 may receive a plurality of input signals including signals generated by sensors 46 and 52, and generate a plurality of output signals including those used to control and/or provide data to magnetic field generator assembly 44 and display 32.

In accordance with the present teachings, ECU 56 may be configured with programming instructions from a computer program (e.g., software) to implement a method for navigating a medical device 14 within body 16. The program may be stored in a computer storage medium such as a memory (not shown) that is internal to ECU 56 or external to ECU 56, and may be pre-installed in the memory or obtained from a computer storage medium external to ECU 56 including from various types of portable media (e.g., compact discs, flash drives, etc.) or file servers or other computing devices accessible through a telecommunications network.

Figure 3:
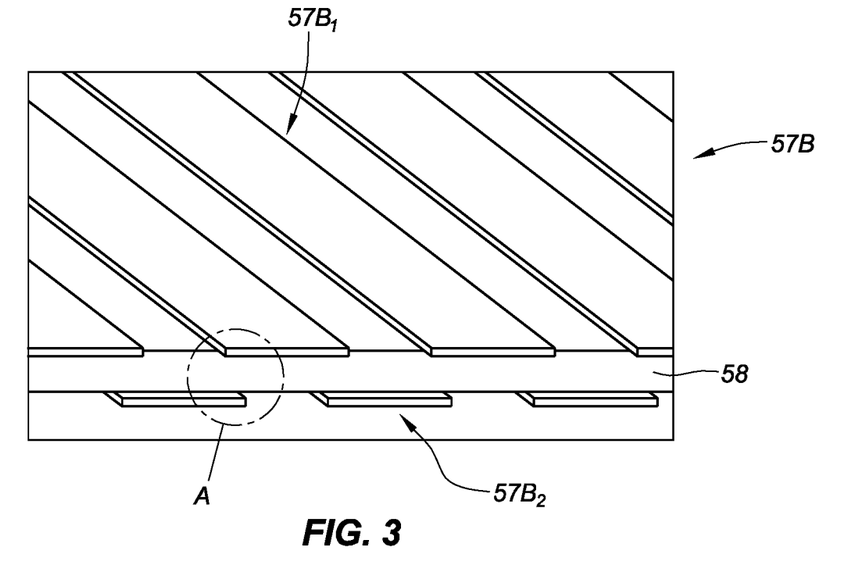
FIG. 3 is an enlarged cross-sectional view of an embodiment of a multi-layer interlacing flat coil transmitter.

In an embodiment, the magnetic field transmitters forming generator assembly 44 may include multi-layer interlacing flat coils, such as the transmitter 57B, an enlarged cross-sectional view of which is shown in FIG. 3. Transmitter 57B includes two coil layers, $57B_1$ and $57B_2$, located on either side of a dielectric substrate layer 58. The dielectric substrate layer 58 prevents current from "short circuiting" between the two coil layers, $57B_1$ and $57B_2$. Because the coils in layer $57B_1$ are located in between the coils of layer $57B_2$ (i.e., the coil layers are interlaced), the visibility of these coil layers is reduced in an X-ray image. In other words, there are no gaps between adjacent turns of coil wires because layer $57B_1$ fills in the gaps created by layer $57B_2$ and vice versa. As can be seen in area A of FIG. 3, there is minimal overlap between the edge of each coil in layer $57B_1$ and the edge of each interlacing coil in layer $57B_2$, which results in homogenicity on an x-ray image. The homogenicity, in turn, results in reduced x-ray image interference (as opposed to stacked coils, for example). In an alternative embodiment, there can be small gaps between the coils in layers $57B_1$ and $57B_2$. In this case, isolated patterns of a conductive element (e.g., copper, aluminum, graphene, or magnesium, for example) with the same thickness as the coils can be used to fill the gaps. The isolated patterns of the conductive element can be sufficiently small so as to minimize eddy currents generated by the magnetic field.

In addition to providing minimal x-ray image interference, the interlaced arrangement of coils described above also provides increased magnetic strength due to the multiple layers of coils (versus a single layer of coils). In an embodiment, the magnetic strength provided by coils in a dual-layer, interlaced arrangement can be approximately twice that of single layer coils. For example, the strength of the magnetic field provided by coils in a dual-layer, interlace arrangement can be in the range of hundreds of micro Tesla. The two interlaced coil layers, $57B_1$ and $57B_2$, are spun in the same direction so as to allow the magnetic field to be transmitted in a single direction.

Figure 4:
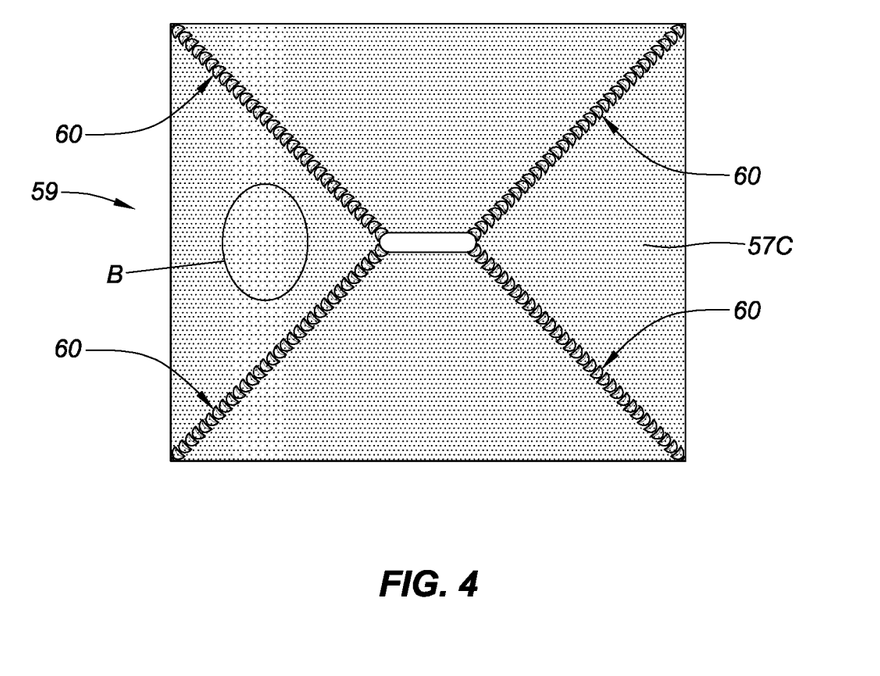
FIG. 4 is an enlarged isometric view of an x-ray image of another embodiment of a multi-layer interlacing flat coil transmitter.

Turning to FIG. 4, an enlarged isometric view of an x-ray image 59 of a single multi-layer interlacing flat coil transmitter 57C is shown. In this embodiment, the individual coils are not visible or barely visible over large portions of the transmitter 57C due to their interlacing arrangement, as described above with respect to FIG. 3. For example, area B represents an area of the x-ray image 59 in which straight or unbent coil traces appear to be uniformly opaque. Thus, area B represents an ideal imaging location. On the other hand, artifact 60 appears on the x-ray image 59 at where the rectangular coils bend and segments of different coil layers cross one under another, leaving gaps 61 (see FIGS. 5A and 6A). In an embodiment, it is possible to eliminate the artifact 60 with additional coil layers to fill the gaps 61 (which appear as artifact 60) created when the multiple layers of the transmitter coil cross under one another. In another embodiment, the gaps 61 can be filled with isolated patterns of conducting elements having approximately the same x-ray absorption properties as the coil traces of the transmitter 57C. These fillers can reduce the artifact visibility in an x-ray image.

Several different manufacturing options exist for the multi-layer interlacing flat coil transmitters 57B and 57C discussed above. The first is printed circuit board (PCB) technology, which provides the advantage of using a repeatable manufacturing process to produce transmitters with identical electrical properties. This method can significantly reduce the need for dedicated calibration procedures. Other options for manufacturing these transmitters include laser cutting using laser micro-machining, 3D printing, direct metal laser sintering (DMLS), and chemical etching. Furthermore, interconnection between individual coil layers may be required to achieve a continuous coil structure. Several options exist for performing this interconnection. For example, microdrilling can be used for the multi-layer structure in target connection locations. Any holes created in the process can be filled with conductive material, such as copper, aluminum, graphene, or magnesium. In addition, a hot bar soldering process using anisotropic conductive film can be used to interconnect the coil layers in the Z direction only. Finally, a wire wrap of the start/end connections of the coils of different layers can be used.

Figure 5A:
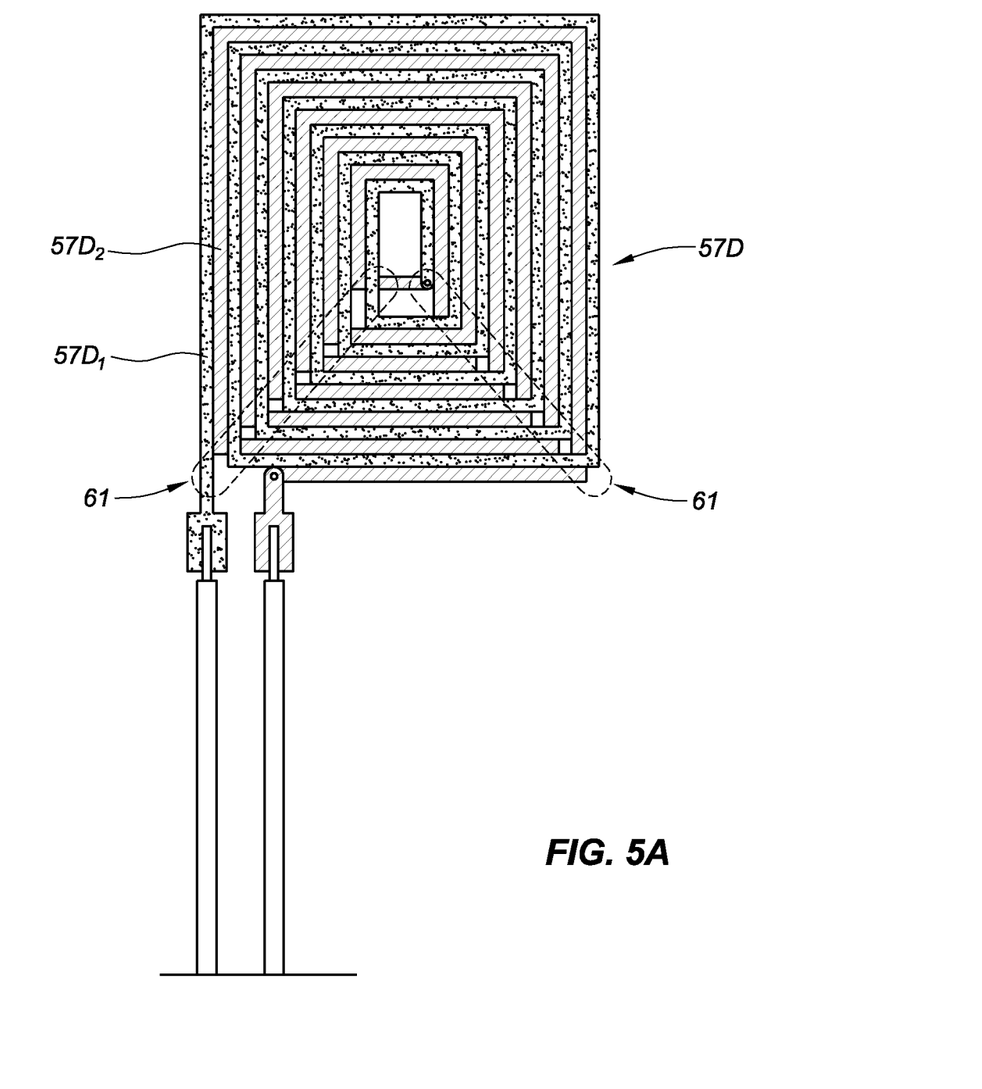
FIG. 5A is a top view of another embodiment of a multi-layer interlaced flat coil transmitter.
Figure 5B:
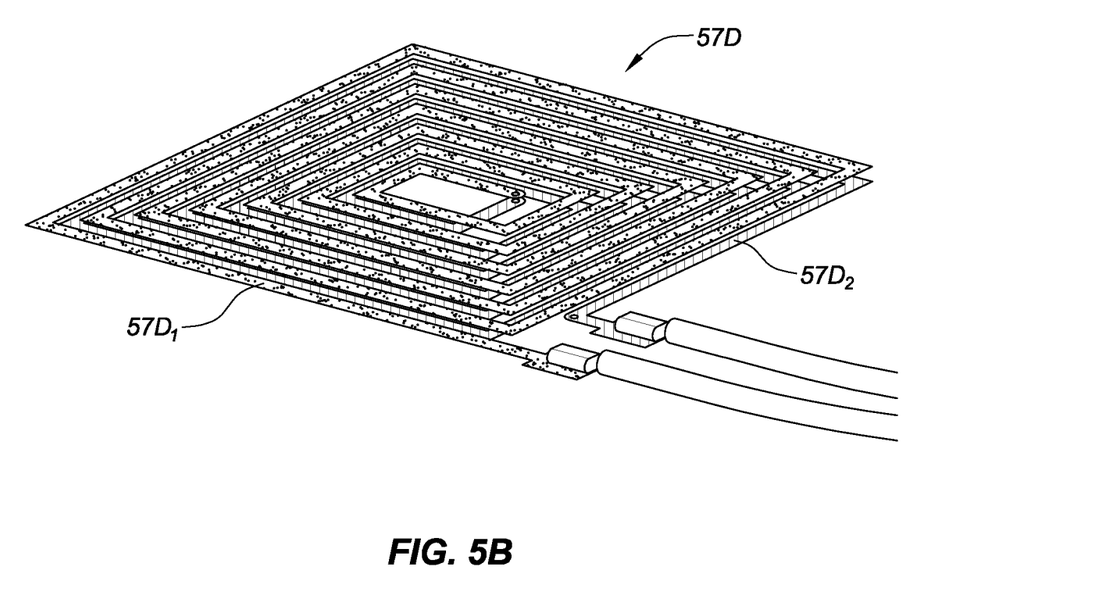
FIG. 5B is a perspective view of the multi-layer interlaced flat coil transmitter shown in FIG. 5A.

FIGS. 5A and 5B illustrate a top view and a perspective view, respectively, of another embodiment of a single, double-layered, interlaced transmitter 57D with electromagnetic current running through coils toward ($57D_1$) and away from ($57D_2$) the transmitter 57D. The dielectric layer 58, which is invisible in x-ray images, is not shown these figures. As is apparent from FIGS. 5A and 5B, the central axes (not shown) of each coil layer can be approximately the same but slightly offset. Referring to FIG. 5A, artifact-producing regions 61 (discussed above with respect to FIG. 4) can be seen in the rectangular transmitter 57D, where one coil layer ($57D_2$) passes under the other coil layer ($57D_1$).

Figure 6A:
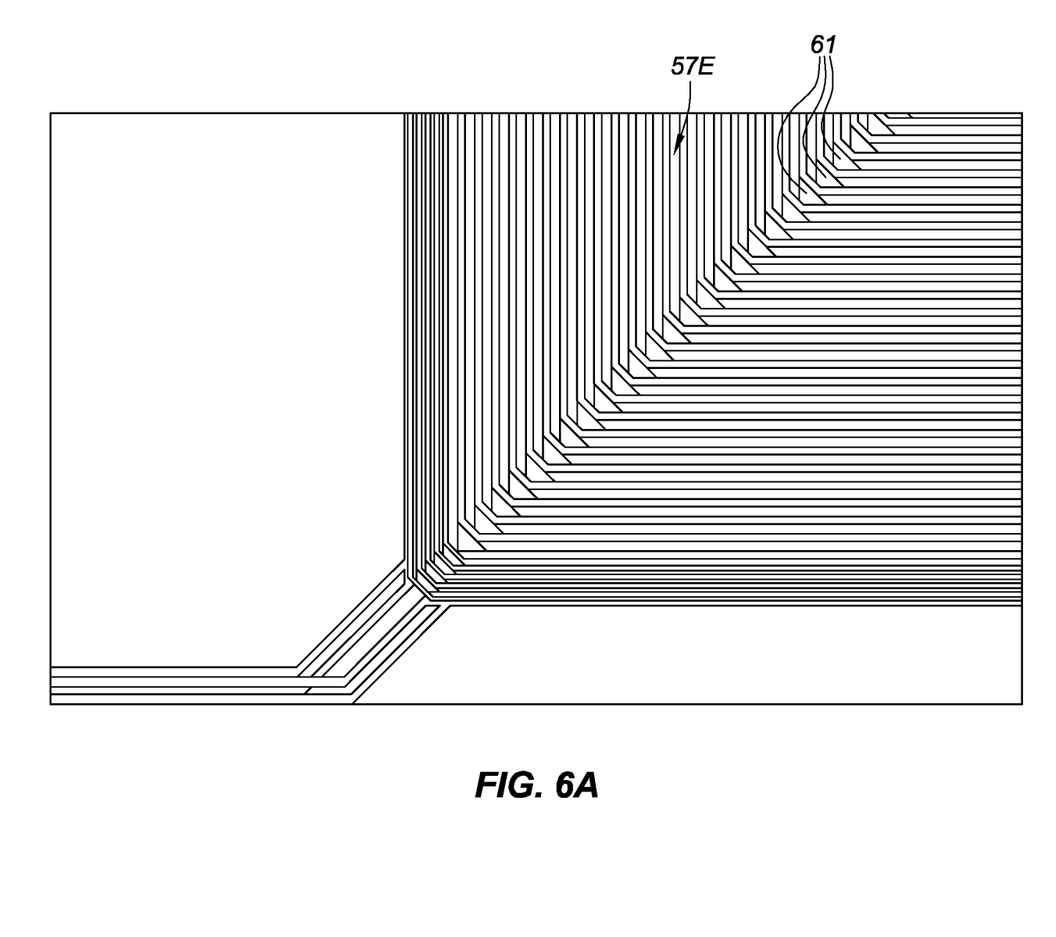
FIG. 6A is a top view of another embodiment of a multi-layer interlaced flat coil transmitter, including artifact-producing regions.
Figure 6B:
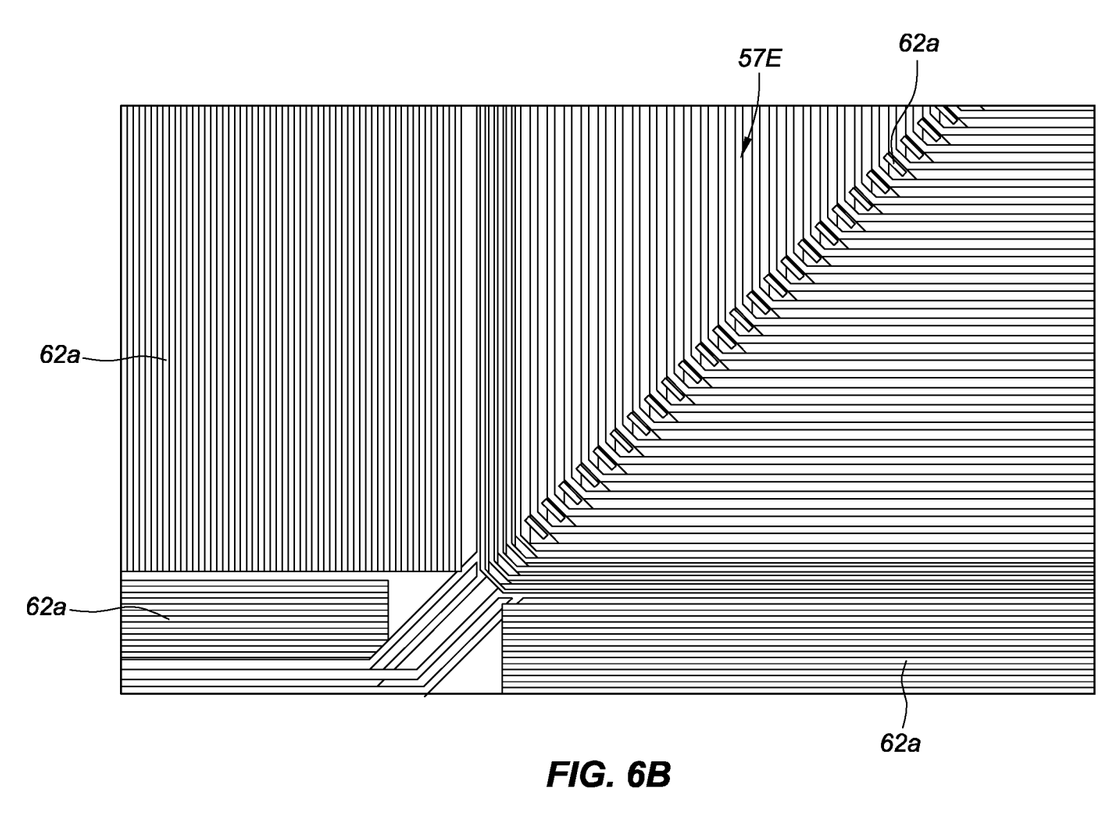
FIG. 6B is a top view of the multi-layer interlaced flat coil transmitter of FIG. 6A, including an example of isolated coil patterns used as a filler to reduce the appearance of artifact on an x-ray image.
Figure 6C:
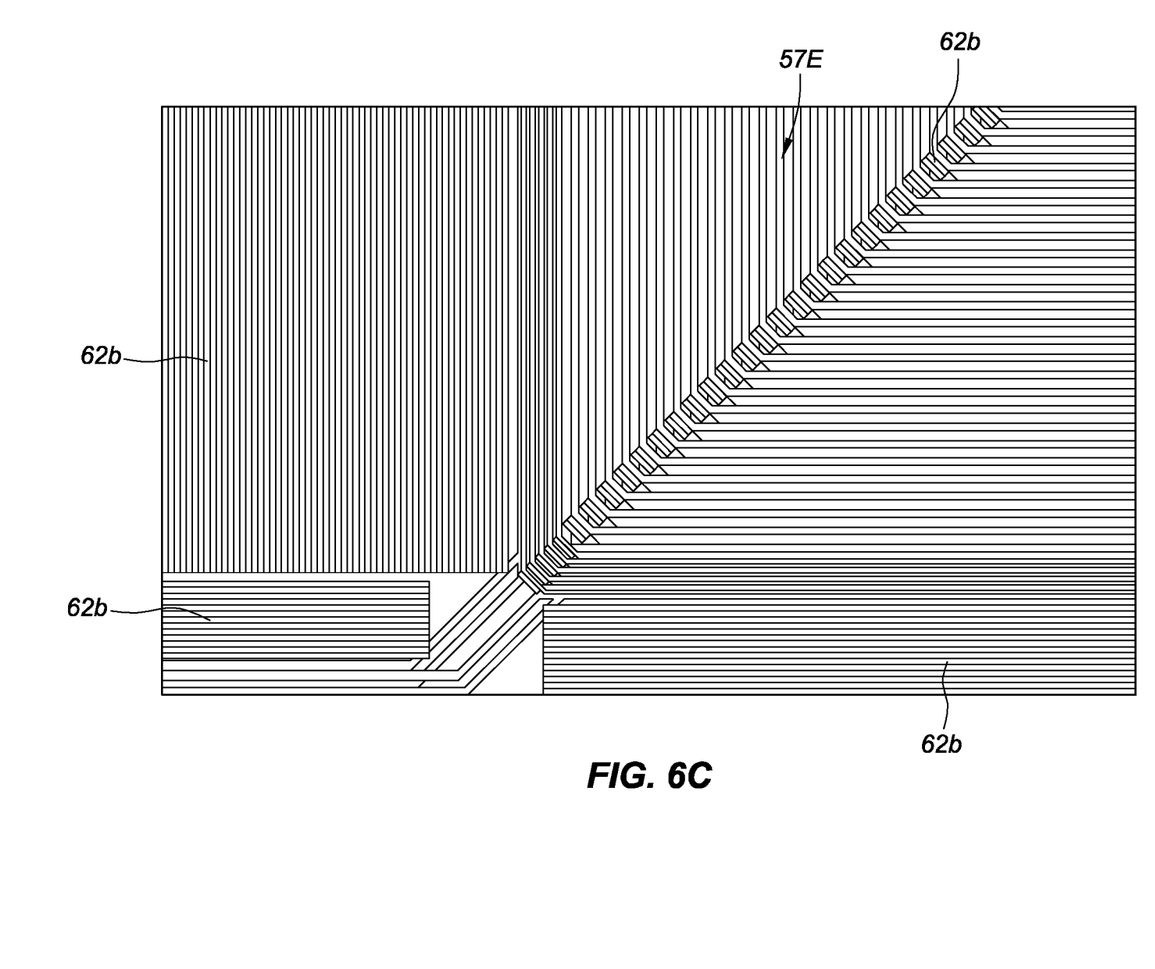
FIG. 6C is a top view of the multi-layer interlaced flat coil transmitter of FIG. 6A, including another example of isolated coil patterns used as a filler to reduce the appearance of artifact on an x-ray image.

FIGS. 6A-C illustrate another embodiment of a single multi-layer interlacing flat coil transmitter 57E. As discussed above with respect to FIGS. 4 and 5A, artifact 60 is created on x-ray images by gaps 61 that are created where rectangular coils bend and one coil layer passes under another. FIG. 6B illustrates an example of an isolated coil pattern 62a that can be used to fill the gaps 61 and reduce the appearance of artifact on x-ray images. FIG. 6C illustrates another embodiment of an isolated coil pattern 62b that can be used to fill the gaps 61 and reduce the appearance of artifact on x-ray images.

Although several embodiments have been described above with a certain degree of particularity, those skilled in the art could make numerous alterations to the disclosed embodiments without departing from the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A magnetic field generating assembly, configured to be associated with a table supporting a body, the assembly comprising:
   a first plurality of elongate conductive elements arranged in a first plane, wherein each of the first plurality of elongate conductive element winds around a first central axis, extending perpendicular to the first plane, in a first spiral formation; and
   a second plurality of elongate conductive elements arranged in a second plane, the second plane being substantially parallel to the first plane, wherein each of the second plurality of elongate conductive element winds around a second central axis, extending perpendicular to the second plane, in a second spiral formation; and an isolated pattern of conductive elements;

wherein each of the first and second spiral formations is rectangular in shape;

wherein each of the first plurality of elongate conductive elements is interlaced with a corresponding one of the second plurality of elongate elements;

wherein each of the first plurality of elongate conductive elements is electrically connected to the corresponding one of the second plurality of elongate conductive elements; and wherein each turn of the first spiral formation is located directly opposite a corresponding gap between successive turns of the second spiral formation in an unbending portion of the rectangular first and second spiral formations, wherein gaps are created at bended portions of the rectangular first and second spiral formations and wherein the isolated pattern of conductive elements fills the gaps between each of the first plurality of elongate conductive elements and each of the second plurality of elongate conductive elements, wherein a width of each of the first plurality of elongate conductive elements is equal to or greater than a width of the corresponding gap.

2. The assembly of claim 1, wherein a dielectric substrate layer separates the first plane and the second plane.

3. The assembly of claim 1, wherein the first spiral formation is wound in a same direction as the second spiral formation.

4. The assembly of claim 1, wherein a first magnetic field generated by a combination of the first and second pluralities of elongate conductive elements is stronger than each of a second magnetic field generated by the first plurality of elongate conductive elements alone and a third magnetic field generated by the second plurality of elongate conductive elements alone.

5. The assembly of claim 1, wherein the first and second pluralities of elongate conductive elements each comprise at least three elongate conductive elements.

6. The assembly of claim 1, wherein the first and second pluralities of elongate conductive elements each comprise at least nine elongate conductive elements.

7. The assembly of claim 1, wherein the first and second pluralities of elongate conductive elements are configured to minimally obstruct images of an object obtained using x-ray fluoroscopy, where x-rays are passed through the first and second pluralities of elongate conductive elements, and where the object is located over an unbending portion of each of the first and second pluralities of conductive elements.

8. The assembly of claim 1, wherein the first and second pluralities of elongate conductive elements comprise at least one of the following: aluminum, copper, graphene, and magnesium.

9. The assembly of claim 1, wherein the first and second pluralities of elongate conductive elements are formed using printed circuit board technology.

10. The assembly of claim 1, wherein the first and second pluralities of elongate conductive elements are located within a housing.

11. The assembly of claim 1, wherein the housing comprises carbon fiber.

12. The assembly of claim 1, wherein the first and second pluralities of elongate conductive elements are configured to be located above, below, or within the table.

13. The assembly of claim 1, wherein the first central axis is slightly offset from the second central axis.

14. The assembly of claim 1, wherein the first and second pluralities of elongate conductive elements are configured to minimally obstruct images obtained using x-ray fluoroscopy, where x-rays are passed through the first and second pluralities of elongate conductive elements.

15. The assembly of claim 14, wherein the first and second pluralities of elongate conductive elements are configured to appear homogenous in the images obtained using x-ray fluoroscopy.

16. A magnetic field generating assembly, configured to be associated with a table supporting a body, the assembly comprising:

a first plurality of elongate conductive elements arranged in a first plane, wherein each of the first plurality of elongate conductive element winds around a first central axis, extending perpendicular to the first plane, in a first spiral formation; and a second plurality of elongate conductive elements arranged in a second plane, the second plane being substantially parallel to the first plane, wherein each of the second plurality of elongate conductive element winds around a second central axis, extending perpendicular to the second plane, in a second spiral formation; and an isolated pattern of conductive elements;

wherein each of the first and second spiral formations is rectangular in shape;

wherein each of the first plurality of elongate conductive elements is interlaced with a corresponding one of the second plurality of elongate elements;

wherein each of the first plurality of elongate conductive elements is electrically connected to the corresponding one of the second plurality of elongate conductive elements; and wherein each turn of the first spiral formation is located directly opposite a corresponding gap between successive turns of the second spiral formation in an unbending portion of the rectangular first and second spiral formations, wherein gaps are created at bended portions of the rectangular first and second spiral formations and wherein the isolated pattern of conductive elements fills the gaps between each of the first plurality of elongate conductive elements and each of the second plurality of elongate conductive elements, wherein a width of each of the first plurality of elongate conductive elements is less than a width of the corresponding gap.

17. A medical device navigation system comprising:

a magnetic field generator assembly configured to be used in close proximity to a body undergoing treatment, wherein the magnetic field generator assembly comprises:

a first plurality of elongate conductive elements arranged in a first plane, wherein each of the first plurality of elongate conductive element winds around a first central axis, extending perpendicular to the first plane, in a first rectangular spiral formation; and a second plurality of elongate conductive elements arranged in a second plane, the second plane being substantially parallel to the first plane, wherein each of the second plurality of elongate conductive element winds around a second central axis, extending perpendicular to the second plane, in a second rectangular spiral formation;

a conductive wire connecting the first and second pluralities of conductive elements to a power source;

an isolated pattern of conductive elements;

a control unit capable of controlling current supplied to the first and second pluralities of conductive elements; and a housing surrounding the first and second pluralities of conductive elements;

wherein each of the first plurality of elongate conductive elements is interlaced with a corresponding one of the second plurality of elongate elements;

wherein each of the first plurality of elongate conductive elements is electrically connected to the corresponding one of the second plurality of elongate conductive elements; and wherein each turn of the first plurality of elongate elements is located directly opposite a corresponding gap between successive turns of the second plurality of elongate elements in an unbending portion of the rectangular first and second spiral formations, wherein gaps are created at bended portions of the rectangular first and second spiral formations and wherein the isolated pattern of conductive element fills the gaps between each of the first plurality of elongate conductive elements and each of the second plurality of elongate conductive elements, wherein a width of each of the first plurality of elongate conductive elements is equal to or greater than a width of the corresponding gap.

18. The system of claim 17, wherein the magnetic field generator assembly is further configured to be operatively coupled with the following: i) a table supporting the body; ii) an imaging system comprising a structure movable relative to the body; and iii) a display.

* * * * *